(12) United States Patent
Zhou

(10) Patent No.: US 8,431,735 B2
(45) Date of Patent: Apr. 30, 2013

(54) PROCESSES FOR PREPARING PHARMACEUTICAL GRADE MELPHALANS FROM INDUSTRIAL GRADE REACTANTS

(75) Inventor: Chen Zhou, Baltimore, MD (US)

(73) Assignee: ChemPacific Corporation, Baltimore, MD (US)

( * ) Notice: Subject to any disclaimer, the term of this patent is extended or adjusted under 35 U.S.C. 154(b) by 339 days.

(21) Appl. No.: 12/379,475

(22) Filed: Feb. 23, 2009

(65) Prior Publication Data
US 2012/0190887 A1 Jul. 26, 2012

Related U.S. Application Data

(60) Provisional application No. 61/064,184, filed on Feb. 21, 2008.

(51) Int. Cl.
*C07C 229/42* (2006.01)

(52) U.S. Cl.
USPC .......................................................... 562/449

(58) Field of Classification Search ................... 562/449
See application file for complete search history.

*Primary Examiner* — Peter G O Sullivan
(74) *Attorney, Agent, or Firm* — Jerome J. Norris

(57) ABSTRACT

A four stage inexpensive method of preparing pharmaceutical grade Melphalans of Melphalan 2-HCl, Melphalan HCl and Melphalan by:
reacting N-phthaloyl-4-[bis(2-hydroxyethyl)amino]-phenylalanine ethyl ester with phosphorous oxychloride, reacting the chlorinated product with HCl and alkali hydroxide and purifying, and lyophilizing to obtain Melphalans.

10 Claims, 5 Drawing Sheets

STAGE 3: COVERT TO FREE BASE

STAGE 4: LYOPHILIZATION

PROCESSES FOR PREPARING PHARMACEUTICAL GRADE MELPHALANS FROM INDUSTRIAL GRADE REACTANTS

CLAIM OF PRIORITY UNDER U.S.C. §119

The present Application for patent claims priority to Provisional Application No. 61/064,184 filed Feb. 21, 2008 and is hereby expressly incorporated by reference herein.

BACKGROUND

1. Field

The present invention process relates to the production of pharmaceutical grade Melphalans or p-bis-(2-chloroethyl)-aminophenylalanine, by using industrial grade reactants. Melphalans or p-bis-(2- chloroethyl)-aminophenylalanine is a known antineoplastic that inhibits or prevents the development of neoplasms by checking the maturation and proliferation of malignant cells; and this is true for the D and L forms as well as the racemic or the DL form.

2. The Prior Art

In U.S. Pat. No. 3,032,584 there is disclosed a process for the manufacture of p-bis-(2-chloroethyl)-aminophenylalanine which comprises heating a compound of the general formula:

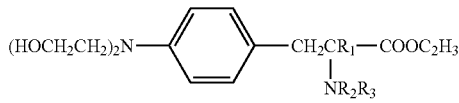

in which $R_1$ is selected from the group consisting of hydrogen and the $COOC_2H_2$ radical, $R_2$ is hydrogen and $R_3$ is selected from the group consisting of CHO and $CH_3$ CO radicals or $R_2$ and $R_3$ together represent the

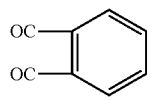

radical, with a chlorinating agent selected from the group consisting of phosphorus oxychloride and thionyl chloride.

Another process for production of p-bis-(2-cloroethyl)-aminophenylalanine is disclosed in U.S. Pat. 3,032,585 and comprises:

treating a solution of N-acetyl-p-nitro-DL-phenylalanine with burcine, separating the optical isomers by crystallization of the brucine salt of the L-isomer, basifying a solution of the brucine salt of the L-isomer to precipitate brucine, removing the brucine, acidifying the solution to produce N-acetyl-p-nitro-L-phenylalanine, subjecting this compound to hydrolysis to produce L-p-nitrophenylalanine, esterifying the carboxyl group of the compound, reacting the ester with phthalic anhydride to form the N-phthaloyl derivative, subjecting this to catalytic hydrogenation to reduce the nitro group to an amino group, treating the amino compound with ethylene oxide to effect hydroxyethylation, and then subjecting the product to chlorination with a chlorinating agent selected from the group consisting of phosphorous oxychloride and thionyl chloride followed by hydrolysis for the removal of the phthaloyl group to produce L-p-bis-(2-chloro-ethyl)-aminophenylalanine.

The processes of these two patents do not utilize inexpensive industrial grade reactants to provide pharmaceutical grade Melphalans.

The use of industrial grade reactants to produce pharmaceutical grade Melphalans would make the products far less expensive and therefore available to patients and governments who would otherwise not be able to afford the same.

SUMMARY

One object is to provide a process for preparing Melphalan 2-HCL by utilizing inexpensive industrial grade reactants to achieve a first manufacturing stage of a chlorination reaction, a second manufacturing stage of hydrolysis/salt formation, a third stage of purification and a fourth stage of salt and lyophilzation to obtain a pharmaceutical grade product.

Another object is to provide a process for preparing Melphalan HCL by utilizing inexpensive industrial grade reactants to achieve a first manufacturing stage of a chlorination reaction, a second manufacturing stage of a hydrolysis/salt formation, a third manufacturing stage of purification and a fourth stage of lyophilization to obtain a pharmaceutical grade product.

A yet further object is to provide a process for preparing Melphalan free base by utilizing inexpensive industrial grade reactants to achieve a first manufacturing stage of a utilizing inexpensive industrial grade reactants to achieve a first manufacturing stage of a chlorination reaction, a second manufacturing stage of hydrolysis/salt formation reaction, a third manufacturing stage of conversion to a free base, and a fourth manufacturing stage of lyophilization to obtain a pharmaceutical grade product.

These and other objects will become apparent by reference to t drawings and the detailed description.

DETAILED DESCRIPTION OF PREFERRED EMBODIMENT

Figure 1:
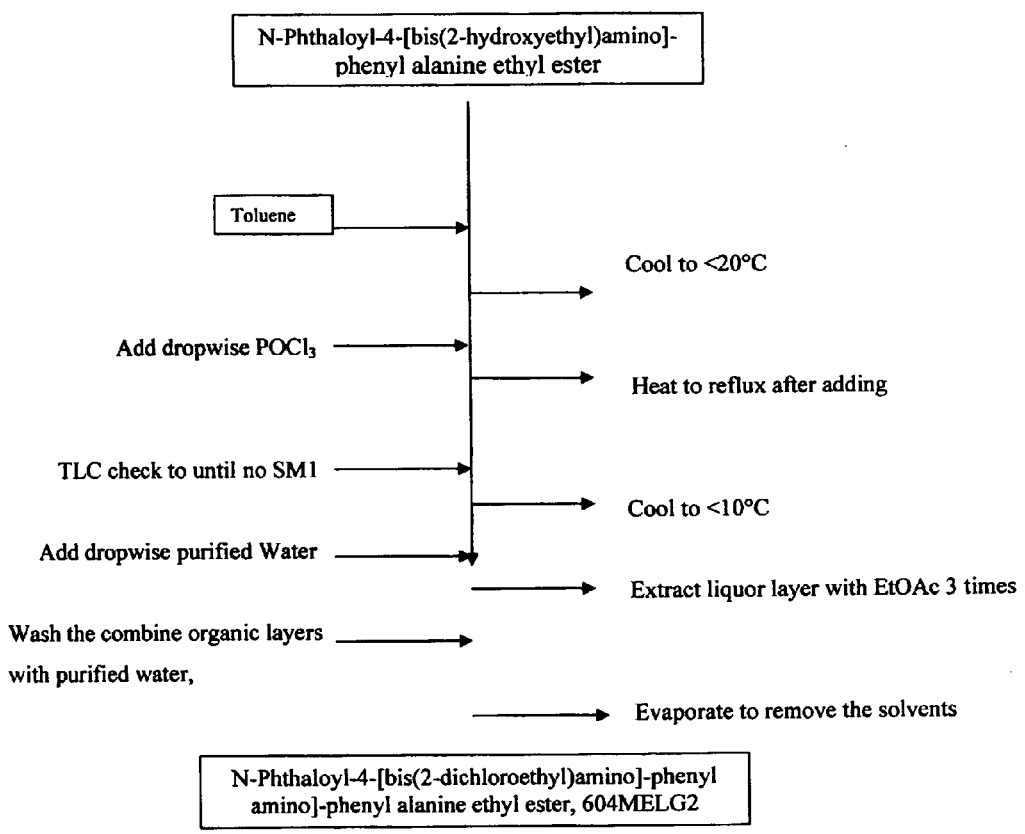
FIG. 1 is a flow chart of manufacturing stage 1 of the clorination reaction.

Manufacturing Process of Melphalan 2 HCl
Chlorination Reaction

| Raw Materials Chemical Name |
| --- |
| N-Phthaloyl-4-[bis(2-hydroxyethyl)amino]-phenyl alanine ethyl ester |
| Phosphorus oxychloride |
| Toluene |
| Ethyl acetate |
| De-ionized water |

Place 2.5 kg of N-Phthaloyl-4-[bis(2-hydroxyethyl) amino]-phenyl alanine ethyl ester), and 10.5 kg of toluene in a 20 L reaction vessel equipped with an agitator and a additional funnel; stir the mixture and cool to below 20° C. Start to drop 2 kg of phosphorus oxychloride from the additional funnel into the mixture. Heat the mixture to reflux after adding. Monitor the reaction by TLC until the N-phthaloyl-4-[bis [2-hydroxyethyl]amino]phenyl alanine ethyl ester is consumed. After reaction, cool the mixture to below 10° C.; add about 6 kg of de-ionized water by dropwise addition to the mixture; stir the mixture for 1 hour while the temperature is controlled to less than 20° C. Transfer the reactant into a 5 L separatory funnel in four portions. Collect the organic layer and extract the aqueous layer with ethyl acetate three times ($1^{st}$: 7 kg; $2^{nd}$ and $3^{rd}$: 5 kg×2). Wash the combined organic layers with 6 kg of de-ionized water. Evaporate the organic layer via a rotary evaporator to remove solvent under vacuum to obtain a green-gray liquor residue. The yield is 2.2~2.5 kg (product weight).

Stage 2: Hydrolysis/Salt Formation

| Raw Materials |
| --- |
| De-ionized water |
| Ammonium hydroxide |
| Conc. hydrochloric acid |

Introduce 4.5 kg of hydrochloric acid into the 20 L of round-bottom flask which contains N-phthaloyl-4-[bis(2-dichloroethyl)amino]-phenyl alanine ethyl ester (2.0~2.5 kg), heat the mixture to 50° C. to make a solution. Transfer the solution into a 20 L reaction vessel equipped with an agitator and an additional funnel. Introduce 4 kg of de-ionized water. Heat the solution to 85~95° C. in the oil bath for 47 hours. Monitor the reaction by HPLC until the green-gray liquor residue and intermediate are consumed. After reaction, cool the mixture down to below 10° C. and keep it at this temperature for 2 hours. Filter the mixture with a Buchner funnel. Wash the filter cake with 2 kg of de-ionized water. Transfer the filtrate into a 20 L reaction vessel in an ice-water bath. Adjust the pH of the filtrate to 1.5 with ammonium hydroxide. Stir the solution for 1~2 hours to form a precipitate. Filter the mixture with a Buchner funnel to obtain the product. The yield is 1.0~1.5 kg (product weight).

Stage 3: Purification

| Raw Materials Chemical Name |
| --- |
| De-ionized water |
| Ammonium hydroxide |
| Conc. hydrochloride acid |
| Isopropyl ether |
| Active charcoal |

Place stage 2 product ($N_1$=1.0~1.5 kg) into a 3 L three-neck round bottom flask equipped with a mechanical stirrer and an additional funnel. Adjust the pH<1 by adding 2.5M HCl. Heat the mixture to 50° C. to dissolve the stage 2 product. Add active charcoal ($1^{st}$: 0.15×$N_1$; $2^{nd}$41: 0.2×$N_2$) to the solution and keep the solution at 60~70° C. for 30 mins. Filter off the solids and wash the solids with de-ionized water ($1^{st}$:0.05× $N_1$; $2^{nd}$: 0.13×$N_2$). Transfer the filtrate into a 5 L three-neck flask and cool the solution to less than 10° C. in an ice-water bath while stirring. Adjust the pH ($1^{st}$: to 1.5; $2^{nd}$: to <1.0) by adding ammonium hydroxide. Filter the mixture after stirring it for 30 mins. Wash the cake with the de-ionized water ($1^{st}$:0.2×$N_1$;$2^{nd}$:2×0.5 $N_2$); slurry the cake with isopropyl ether (1.6×$N_2$) and filter the slurry to give a wet product ($N_2$). Repeat to purify using the above procedure once more to give a wet product ($N_3$) except that the amount of solvents and reagents are changed; the final pH is adjusted by ammonium hydroxide so that it is changed to <1.0. Place the wet product in several vacuum flasks (~100 g wet product/500 mL vacuum flask). Add 70~80 mL of distilled water into each flask. Mix and then pre-lyophilize for about 5 hours and then lyophilize for 60~70 hours. Mill the sample to provide the product. The yield of the product is 260~280 g (product weight).

Stage 4: Formation of 2HCl Salt and Lyophilization

| Raw Materials Chemical Name |
| --- |
| 4N HCl |
| Melphalan 2HCl |

Place 100~500 g of Melphalan HCl (IM1036) into a flask. Add 4N HCl until most of the solids are dissolved while stirring. Stir the mixture for more than 10 mins. Filter the mixture with a Millipor® all-glass 47 mm microfiltration assembly with nylon membrane. Rinse the solid with 4N HCl; combine the filtrate and wash to give a clear pale-yellow solution. Transfer the solution into several vacuum flasks. Swirl the vacuum flasks gently in a dry-ice/acetone bath. The cooling process will take more than 30 min. until the liquid is completely frozen. Mount the flasks to a lyophilizer with the pressure preset at 225 mmHg and temperature at <−40° C. The freeze-drying process continues for more than 48 hours until the water content meets the specification requirement. Release the vacuum and weigh the product. The product is packed in the polypropylene bags inside a sealed aluminum pouch and stored at 2~8° C. in a refrigerator, to protect from light and moisture. The yield is 90~95% of theoretical yield.

Reprocessing of Melphalan 2 HCl

If Melphalan 2 HCl API does not conform to specifications such as appearance, or purity as reflected by HPLC assay, then the purification, Lyophilization and 2 HCl formation procedures as described in Stages 3 and 4 are again used to refine the product. After reprocessing, the initial batch number is suffixed with an "R" denoting the reprocessing operation. The cause of OOS will be investigated and remedial steps will be taken.

The stage 1 Manufacturing of the Chlorination Reaction is shown in FIG. 1.

Stage 1: Chlorination Reaction

| Raw Materials Chemical Name |
| --- |
| N-Phthaloyl-4-[bis(2-hydroxyethyl)amino]-phenyl alanine ethyl ester |
| Phosphorus oxychloride |
| Toluene |
| Ethyl acetate |
| De-ionized water |

Place 2.5 kg of N-Phthaloyl-4-[bis(2-hydroxyethyl) amino]-phenyl alanine ethyl ester (604MELG1), and 10.5 kg of toluene (601MBXX) in a 20 L reaction vessel equipped with an agitator and an additional funnel; stir the mixture and cool it to below 20° C. Start to drop 2kg of phosphorus oxychloride from the additional funnel into the mixture and heat the mixture to reflux after the addition. Monitor the reaction by TLC until the raw material (604MELG1) is consumed. After reaction, cool the mixture to below 10° C.; add about 6 kg of de-ionized water by dropwise addition to the mixture; stir the mixture for 1 hour while the temperature is controlled at less than 20° C. Transfer the reactant into a 5 L separatory funnel in four portions. Collect the organic layer and extract the aqueous layer with ethyl acetate three times ($1^{st}$: 7 kg; $2^{nd}$ and $3^{rd}$: 5 kg×2). Wash the combined organic layers with 6 kg of de-ionized water. Evaporate the organic layer via a rotary evaporator to remove the solvent under vacuum to get the green-gray liquor residue (604MELG2). The yield is 2.2~2.5 kg (product weight).

Figure 2:
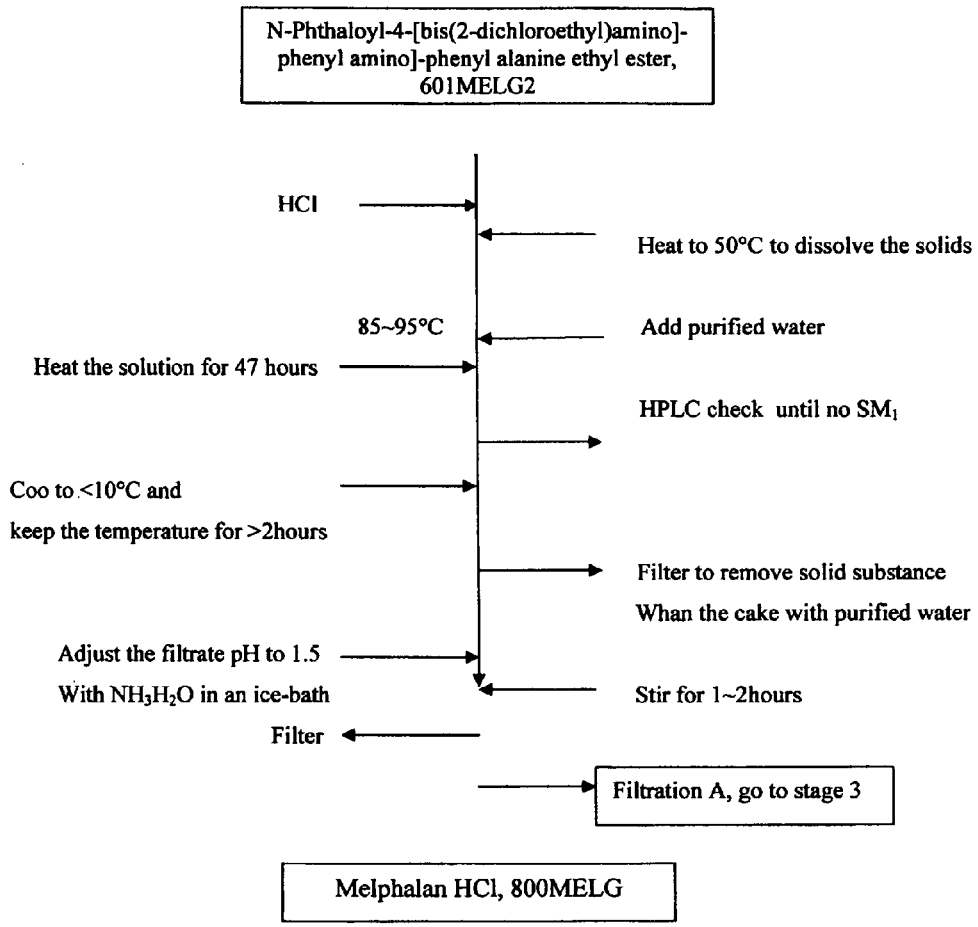
FIG. 2 is a flow chart of the stage 2 hydrolysis/salt formation reaction.

The Stage 2: Hydrolysis/Salt Formation Reaction is shown in FIG. 2.

| Raw Materials |
| --- |
| Raw Materials |
| De-ionized water |
| Ammonium hydroxide |
| Conc. hydrochloric acid |

Introduce 4.5 kg of hydrochloride acid into the 20 L of round-bottom flask which contained N-phthaloyl-4-[bis(2-dichloroethyl)amino]-phenyl alanine ethyl ester (2.0~2.5 kg), 604MELG1. Heat the mixture to 50° C. obtain a solution. Transfer the solution into a 20 L reaction vessel equipped with an agitator and an additional funnel. Then introduce 4 kg of de-ionized water. Heat the solution to 85~95° C. in the oil bath for 47 hours. Monitor the reaction by HPLC until the raw material (604MELG2) and intermediate are consumed. After reaction, cool the mixture down to below 10° C. and then keep it at this temperature for 2 hours. Filter the mixture with a Buchner funnel. Wash the filter cake with 2 kg of de-ionized water. Transfer the filtrate into a 20 L Reaction vessel in an ice-water bath. Adjust the pH of the filtrate to 1.5 with ammonium hydroxide. Stir the solution for 1~2 hours until the precipitation is completed. Filter the mixture with a Buchner funnel to get the product (800MELG). The yield is 1.0~1.5 kg (product weight).

Stage 3: Purification

| Raw Materials |
| --- |
| Chemical Name |
| De-ionized water |
| Ammonium hydroxide |
| Conc. hydrochloride acid |
| Diethyl ether |
| Active charcoal |

Place stage 2 product ($N_1$=1.0~1.5 kg) into a 3 L three-necked round bottom flask equipped with a mechanical stirrer and an additional funnel. Adjust the pH<1 by adding 2.5M HCl. Heat the mixture to 50° C. to dissolve the stage 2 product. Add active charcoal ($1^{st}$: 0.15×$N_1$; $2^{nd n}$: 0.2×$N_2$) to the solution and keep the solution at 60~70° C. for 30 mins. Filter off the solids and wash the solids with de-ionized water ($1^{st}$: 0.05×$N_1$; $2^{nd}$: 0.13×$N_2$). Transfer the filtrate into a 5 L three-necked flask and cool the solution to less than 10° C. in an ice-water bath while stirring. Adjust the pH ($1^{st}$: to 1.5; $2^{nd}$: to <1.0) by adding ammonium hydroxide. Filter the mixture after stirring it for 30 mins. Wash the cake with de-ionized water ($1^{st}$:0.2×$N_1$; $2^{nd}$:4×0.2$N_2$); slurry the cake with diethyl ether and filter the slurry to obtain a wet product ($N_2$). Repeat the above procedure one more time to obtain a wet product ($N_3$) except that the amount of solvents and reagents are changed; the final pH adjusted by ammonium hydroxide is changed to <1.0. Place the wet product in several vacuum flasks (~100 g wet product/500 mL vacuum flask). Add 70~80 mL of distilled water into each flask. Mix well and then pre-lyophilize for about 5 hours and then lyophilize for 60~70 hours. Mill the sample to obtain the product, 800MELG (US code: IM1036).

The product yield is 260~280 g (product weight).

Stage 4: Lyophilization

| Raw Materials |
| --- |
| Chemical Name |
| Melphalan HCl |

Place 200~1000 g of Melphalan HCl (IM1036) into the vacuum flask, and quickly mount the vacuum flask to a Lyophilizer with the pressure preset at 225 mmHg and temperature at <−40° C. The freeze-drying process is continued overnight until the water content meets the specification requirement. The vacuum is released and the product is weighed. The product is packed in polypropylene bags inside a sealed aluminum pouch and stored at 2~8° C. in a refrigerator, to protect it from light and moisture. The yield is 96~99% of theoretical yield.

Reprocessing of Melphalan HCl

If the Melphalan HCl API does not conform to specifications such as appearance, or purity as reflected by HPLC assay, then the crystallization and lyophilization procedures as described in Stags 3 and 4 are again used to refine the product. After reprocessing, the initial batch number is suffixed with an "R" denoting the reprocessing operation. The cause of OOS is investigated and remedial steps are then taken.

To a 20 L three-neck round bottom flask equipped with an agitator, place 2.5 kg of N-Phthaloyl-4-[bis(2-hydroxyethyl)amino]-phenyl alanine ethyl ester and 10.5 kg of toluene. Stir and cool the mixture to <20° C. and add phosphorus oxychloride oxide dropwise. After the addition is completed, heat the mixture to reflux until no $SM_1$ is found on the TLC plate. Cool the reactant to <10° C. Add 6 kg of purified water dropwise while the temperature is maintained at <20° C. Pour the reactant solution into a separatory funnel, extract the solution with ethyl acetate three times ($1^{st}$: 7 kg; $2^{nd}$: 5 kg; $3^{rd}$: 5 kg). Combine organic layers and then wash the solution with 6 kg of purified water. Evaporate the solvents to obtain a brown-yellow liquid residue.

To a 20-L round bottom flask is added 2.5 kg of N-Phthaloyl-4-[bis(2-dichloroethyl)amino]-phenyl amino]-phenyl alanine ethyl ester and 9 kg of hydrochloride acid. Heat the mixture to 50° C. Add 8 kg of purified water until the material is dissolved completely. Transfer the solution to a 20-L reactor. Heat the solution to reflux for more than 7 hours. The reaction is monitored by HPLC for completion. Cool the reactant below 10° C. while stirring for 2 hours. Filter with a Buchner funnel and wash the cake with 2 kg of purified water. Transfer the filtrate to a 20-L reactor. Adjust the pH of the filtrate to 1.5 with ammonium hydroxide in an ice bath. Stir the mixture for 1~2 hours until a solid is formed completely. The solid is collected in a Buchner funnel to give Melphalan HCl and filtration (A).

Figure 3A:
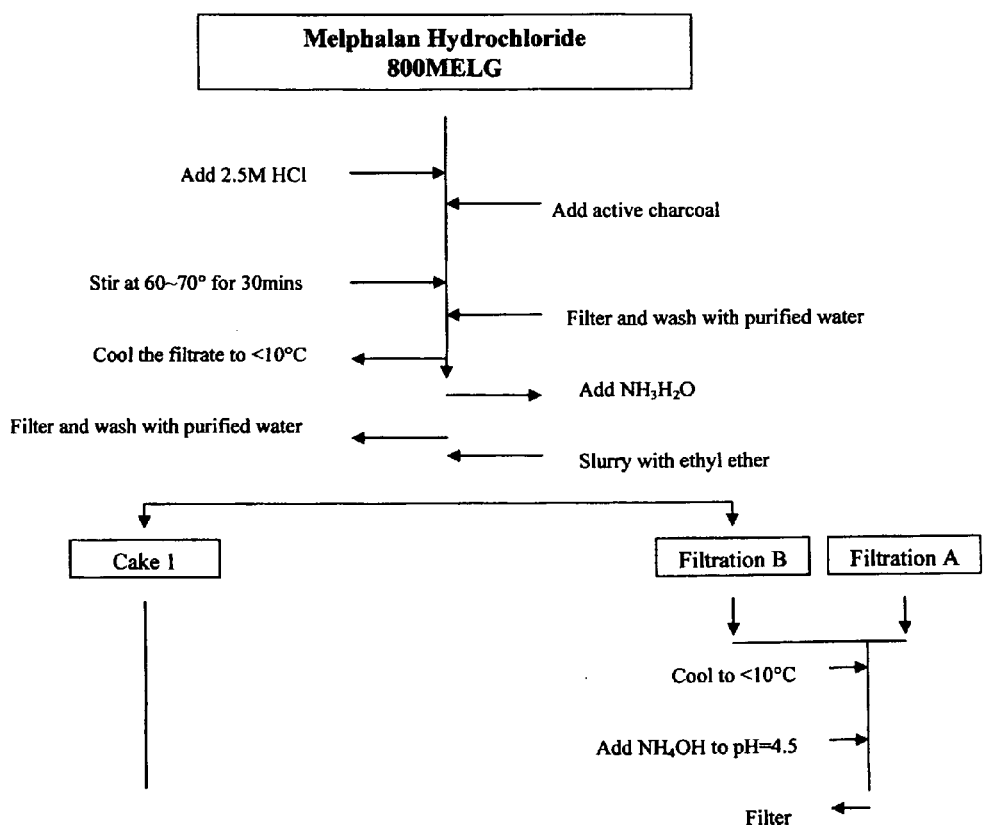
FIG. 3A-3B is a flow chart of the stage 3 conversion to a free base.
Figure 3B:
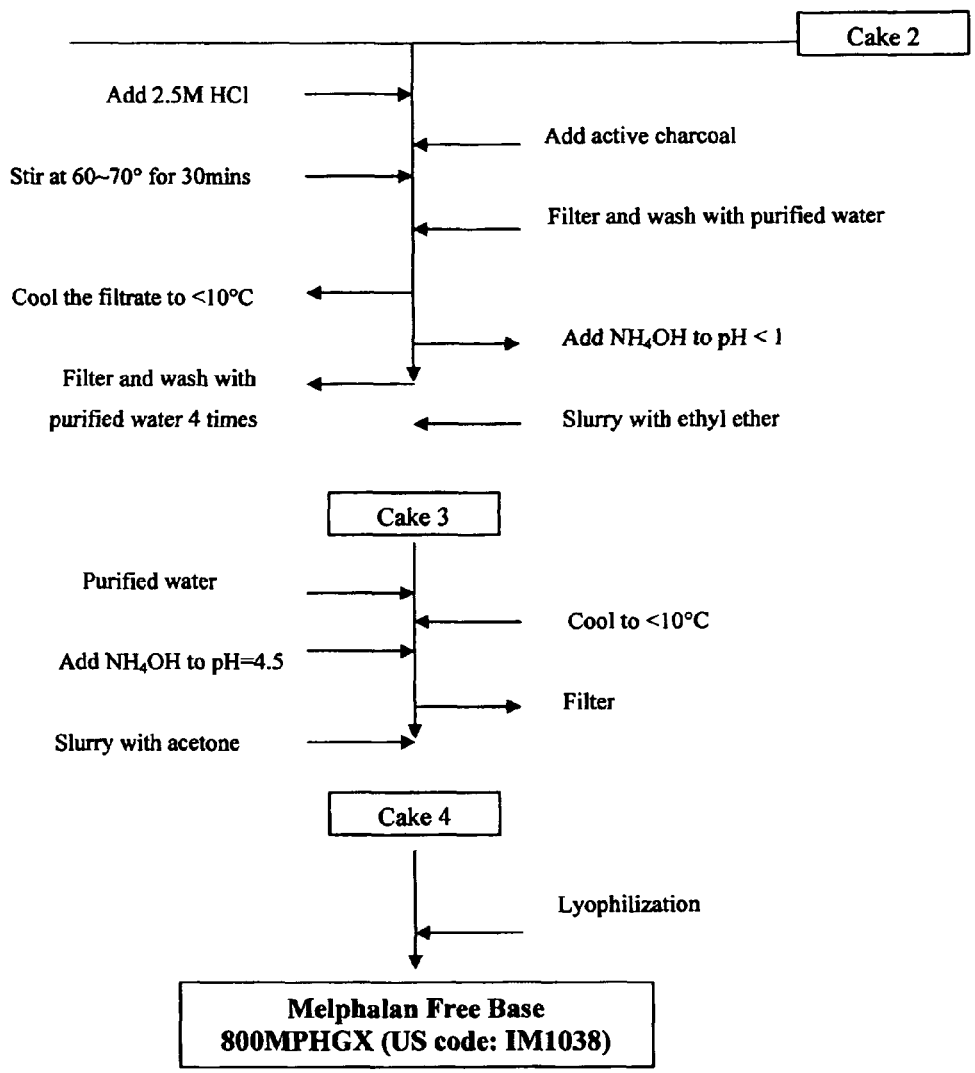

Stage 3 Coverting to the Free Base is shown in FIGS. 3A and 3B.

To a 10-L round bottom flask is added $N_{SM3}$ (g) of Melphalan HCl. Adjust the pH of the solution to <1 by adding 2.5M hydrochloride acid. Heat the mixture to 50° C. Add 0.15$N_{SM3}$ (g) of active charcoal after the solids are dissolved. Stir the mixture at 60~70° for 30 mins. Filter with Buchner funnel and wash the cake with 2$N_{SM3}$ (g) of purified water. Transfer the filtrate to a 20-L reactor and cool the solution to <10° C. Adjust the pH of the filtrate to 1.5 with ammonium hydroxide in an ice bath. Stir the mixture for 30 mins. Collect the solid on a Buchner funnel and wash it with 0.25$N_{SM3}$ (g) of purified water. Stir the cake with 1.6$N_{SM3}$ (g) of ethyl ether and filter the slurry to get a wet cake (1) and filtration (B). Combine the filtration (A and B) from above and the last operation in stage 2 in a 15 L bucket. Cool the filtrate to <10° C. Adjust the pH of the filtrate to 4.5 with ammonium hydroxide in an ice bath. Collect the solid on a Buchner funnel. Transfer the cake (Nc, g) into a 10L bucket and then add Nc (g) of 2.5M HCl. Stir to dissolve the solids. Cool the solution to <10° C. Adjust the pH of the filtrate to 1.5 with ammonium hydroxide in an ice bath. Collect the solid with a Buchner funnel to get the wet cake (2).

Place the wet product (1) and (2) (total=N, g) in a 10L reactor. Add 3.5N (g) of 2.5M HCl. Heat the mixture to 50° C. Add 0.2$N_{SM3}$ (g) of active charcoal after the solids are dissolved. Stir the mixture at 60~70° for 30 mins. Filter with a Buchner funnel and wash the cake with 0.15N (g) of purified water. Transfer the filtrate to a 20-L reactor and cool the solution to <10° C. Adjust the pH of the filtrate to <1.0 with ammonium hydroxide in an ice bath. Collect the solid on a Buchner funnel and wash it with 0.5N (g) of purified water four times. Stir the filter cake with 1.6N(g) of ethyl ether and filter the slurry to give the wet product (3). Add the purified water into the wet cake (3) and then cool the solution to <10° C. Adjust the pH of the filtrate to 4.5 with ammonium hydroxide in an ice bath. Collect the solid on a Buchner funnel and wash it with 1 kg of purified water four times. Stir the filter cake with 1.6N (g) of acetone and filter the slurry to give the wet cake (4).

Place the wet cake (4) in several vacuum flasks (~100 g wet product/500 mL vacuum flask). Add 70~80 mL of purified water into each flask. Mix well and then pre-lyophilize for about 5 hours and then lyophilize for 60~70 hours. Mill the sample to give the Melphalan, 800MPHG (US code: IM1038).

Figure 4:
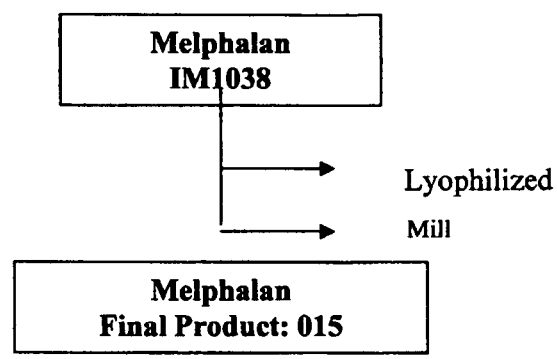
FIG. 4 is a flow chart of the stage 4 lyophilization step.

The Lyophilization Stage is shown in FIG. 4.

Place the IM1038 quickly in 1 L or 2L Vacuum Flasks and mount the Vacuum Flask to a Lyophilizer with pressure preset under $300 \times 10^{-3}$ mbar or 225 mmHg at <−40° C. Continue the freeze-drying process for overnight until water content is ≦7%. The milling procedures were carried out on a two-hand AtmosBag™, which is put in a hood filled with Nitrogen gas to protect from light and moisture, using a cleaned Mortar. Mill a fraction amount of free base Melphalan (about 20 g) for about 20 minutes each time, and transfer the fine powder into a clean amber bottle after milling each time. After milling all of Melphalan, transfer the fine powder back into the Mortar, then blend together. Blend the mixture with a spoon for ~15 minutes to give a homogenous mixture.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

I claim:

1. A four stage inexpensive method of preparing pharmaceutical grade Melphalan2HCl utilizing industrial grade reactants, comprising:
    a) reacting N-phthaloyl-4-[bis(2-hydroxyethyl) amino]-phenylalanine ethyl ester with phosphorous oxychloride to obtain a chlorinated reaction product;
    b) obtaining a hydrolysis/salt formation precipitate of said chlorinated reaction product by reacting same with hydrochloric acid followed by reaction with an alkali hydroxide;
    c) purifying said hydrolysis/salt formation precipitate by dissolving in hydrochloric acid, adding active charcoal, adding alkali hydroxide, filtering and washing with deionized water, slurrying with isopropyl ether; repeating said purifying step, adding distilled water, lyophilizing and milling to obtain a product; and
    d) obtaining a pharmaceutical grade Melphalan-2HCl by: dissolving the product of step c) adding HCl, freezing until frozen, and lyophilizing.

2. The method of claim 1, wherein steps c) and d) are repeated.

3. The method of claim 1, wherein said alkali hydroxide is ammonium hydroxide.

4. The method of claim 2, where said alkali hydroxide is ammonium hydroxide.

5. A four stage inexpensive method of preparing pharmaceutical grade Melphalan HCl utilizing industrial grade reactants, comprising:
    a) reacting N-phthaloyl-4-[bis(2-hydroxyethyl) amino]-phenylalanine ethyl ester with phosphorous oxychloride to obtain a chlorinated reaction product;
    b) obtaining a hydrolysis/salt formation precipitate of said chlorinated reaction product by reacting same with hydrochloric acid followed by reaction with an alkali hydroxide;
    c) purifying said hydrolysis/salt formation precipitate by dissolving in hydrochloric acid, adding active charcoal, adding alkali hydroxide, filtering and washing in deionized water, slurrying with diethyl ether; repeating said purifying step, adding distilled water, lyophilizing and milling ; and
    d) obtaining a pharmaceutical grade Melphalan HCl by: freezing and lyophilizing.

6. The method of claim 5, wherein steps c) and d) are repeated.

7. The method of claim 5, wherein said alkali hydroxide is ammonium hydroxide.

8. The method of claim 6, wherein said alkali hydroxide is ammonium hydroxide.

9. A four stage inexpensive method of preparing pharmaceutical grade Melphalan utilizing industrial grade reactants, comprising:
    a) reacting N-phthaloyl-4-[bis(2-hydroxyethyl) amino]-phenylalanine ethyl ester with phosphorous oxychloride to obtain a chlorinated reaction product;
    b) obtaining a hydrolysis/salt formation precipitate of said chlorinated reaction product by reacting same with hydrochloric acid followed by reaction with an alkali hydroxide;
    c) converting the Melphalan hydrochloride product of step b) to a free base by: dissolving in hydrochloric acid , adding active charcoal, filtering and washing with water, slurrying in ethyl ether, filtering adjusting the filtrate to a basic pH with an alkali hydroxide, slurrying with ethyl ether cooling filtering, slurrying with acetone, and filtering to obtain a Melphalan free base; and d) lyophilizing said free base, and milling the product to obtain Melphalan.

10. The method of claim 9 wherein said alkali hydroxide is ammonium hydroxide.

\* \* \* \* \*